United States Patent
Jordan et al.

[11] Patent Number: 6,153,777
[45] Date of Patent: *Nov. 28, 2000

[54] SYNTHESIS OF ANSA-METALLOCENE CATALYSTS

[75] Inventors: Richard F. Jordan, Chicago, Ill.; Xingwang Zhang, Iowa City, Iowa

[73] Assignee: University of Iowa Research Foundation, Iowa City, Iowa

[*] Notice: This patent is subject to a terminal disclaimer.

[21] Appl. No.: 09/431,825

[22] Filed: Nov. 2, 1999

[51] Int. Cl.[7] .............................. C07F 17/00; C07F 7/00; C07F 19/00
[52] U.S. Cl. ................................ 556/11; 556/20; 556/43; 556/53; 502/103; 502/117; 526/160; 526/943
[58] Field of Search ................................ 556/11, 20, 43, 556/53; 502/103, 117; 526/160, 943

[56] References Cited

U.S. PATENT DOCUMENTS

| | | | |
|---|---|---|---|
| 5,597,935 | 1/1997 | Jordan et al. | 556/11 |
| 5,616,747 | 4/1997 | Rohrmann et al. | 556/11 |
| 5,847,175 | 12/1998 | Strickler et al. | 556/11 |

FOREIGN PATENT DOCUMENTS 0 745 606 A2  5/1996  European Pat. Off. .

OTHER PUBLICATIONS

Brintzinger, H. H.; Fischer, D.; Mülhaupt, R.; Rieger, B.; Waymouth, R. M. *Angew. Chem., Int. Ed. Engl.* 1995, 34, 1143–1170.
Hoveyda, A. H.; Morken, J. P. *Angew. Chem., Int. Ed. Engl.* 1996, 35, 1262–1284.
Spaleck, W.; Küber, F.; Winter, A.; Rohrmann, J.; Bachmann, B.; Antberg, M.; Dolle, V.; Paulus, E.F., *Organmetallics* 1994, 13, 954–963.
Stehling, U.; Diebold, J.; Kirsten, R.; Röll, W.; Brintzinger, H. H.; Jüngling, S.; Mülhaupt, R.; langhauser, F., *Organometallics* 1994, 13, 964–970.
Ellis, W. W.; Hollis, T.K., Odenkirk, W.; Whelan, J.; Ostrander, R.; Rheingold, AS> L.; Bosnich, B., *Organometallics* 1993, 12, 4391–4401.
Diamond, G.M.; Jordan, R.F.; Petersen, J.L.; *Organometallics*, 1996, 15, 4030–4037.
Christopher, J.N.; Jordan, R.F.; Petersen, J.L.; Young, V.G. Jr., *Organometallics* 1997, 16, 3044–3050.

*Primary Examiner*—Porfirio Nazario-Gonzalez
*Attorney, Agent, or Firm*—Zarley, McKee, Thomte, Voorhees & Sease

[57] ABSTRACT

A process of preparing in high yield racemic ansa-metallocene complexes by reacting a chelated bisamide group 4 metal complex with an ansa-bis-cyclopentodrenyl dianion reagent. The meso isomers are not detectable in the reaction product.

50 Claims, 3 Drawing Sheets

SYNTHESIS OF ANSA-METALLOCENE CATALYSTS

BACKGROUND OF THE INVENTION

This invention relates to the field now well established of ansa-metallocenes which are used as catalysts. They are particularly useful as catalysts for the polymerization of α-olefins.

Conventional heterogeneous catalysts such as Ziegler-Natta systems have a variety of active sites, only some of which are stereo-specific. Obtaining a polymer with specific properties can involve a considerable amount of trial and error in order to find the best combination of catalyst, co-catalyst and stereo-regulator. In contrast, however, the active polymerization site in a metallocene catalyst is well defined, and can be modified in a straightforward manner via modification of the cyclopentadienyl ligands, enabling the structure of the polymer to be controlled with far greater precision.

A simple metallocene catalyst for polymerizing ethylene $(C_5H_5)_2ZrCl_2$ which consists of a zirconium atom bound to two chlorine atoms and two cyclopentadienyl rings, and which is activated by co-catalysts such as methylaluminoxane (MAO). During the 1980's, ansa, or bridged, metallocenes, in which the cyclopentadienyl rings are linked by a chemical bridge, were found to be particularly useful for the polymerization of olefins. In particular, ansa-metallocene complexes, when used in combination with a co-catalyst such as methylaluminoxane (MAO), polymerize propylene to highly isotactic polypropylene, highly syndiotactic polypropylene, or atactic polypropylene, depending on the structure of the ansa-metallocene used.

As is well known, isotactic polymers have each pendant group attached to the backbone in the same orientation, whereas in syndiotactic polymers, these groups alternate in their orientations and atactic polymers have a random arrangement of the groups along the backbone. Since the stereochemistry of the polymer has a great effect on its properties, it is desirable to control this feature. Chiral, $C_2$-symmetric ansa-metallocenes produce isotactic polypropylene.

Chiral rac ansa-zirconocene complexes, when activated by MAO or other cocatalysts, are excellent catalysts for isotactic α-olefin polymerization and other stereoselective reactions. Brintzinger, H. H.; Fischer, D.; Mulhaupt, R.; Rieger, B.; Waymouth, R. M., *Angew. Chem., Int. Ed. Engl.*, 1995, 34, 1143. Hoveyda, A. H.; Morken, J. P. *Angew. Chem., Int. Ed. Engl.*, 1996, 35, 1262. Racemic $SiMe_2$-bridged bis-indenyl zirconocenes that contain methyl and aryl substituents at the indenyl 2 and 4 positions, respectively, are among the best metallocene catalysts for the production of high molecular weight, isotactic poly(α-olefins). Spaleck, W.; Küber, F.; Winter, A.; Rohrmann, J.; Bachmann, B.; Antberg, M.; Dolle, V.; Paulus, E. F., *Organonmetallics*, 1994, 13, 954. Stehling, U.; Diebold, J.; Kirsten, R.; Röll, W.; Brintzinger, H. H.; Jüngling, S.; Mülhaupt, R.; Langhauser, F., *Organometallics*, 1994, 12, 964.

While the greatest area of potential use for ansa-metallocene catalysts currently is for polymerization of olefins, such as ethylene and propylene, they also have significant uses as catalysts or catalyst precursors for other reactions where stereo-selectivity is important.

The utility of ansa-metallocene complexes as catalysts for olefin polymerization and other reactions has created a high demand for practical syntheses of ansa-metallocene compounds.

In spite of this demand, current procedures for the synthesis of Group IV (Ti, Zr, Hf) ansa-metallocenes are hampered by low yields and tedious isomer separation and purification steps. Some of these problems have been discussed in Ellis, W. W.; Hollis, T. K.; Odenkirk, W.; Whelan, J.; Ostrander, R.; Rheingold, AS. L.; Bosnich, B. *Organometallics* 1993, 12, 4391. In particular, the synthesis of chiral $C_2$ symmetric ansa-metallocenes typically produces mixtures of desired racemic (rac) and undesired meso isomers and separation of the rac from the meso products is not always possible.

Ansa-zirconocenes are normally synthesized by salt-elimination reactions between bis-indenyl anion reagents and $ZrX_4$ or $ZrX_4L_2$ compounds (L=Lewis base). However, the factors that control chemoselectivity (i.e., metallocene vs. dinuclear products) and diastereoselectivity (i.e., rac/meso selectivity) in these reactions are not well understood, and extensive screening studies of reagents, counterions, solvents, use of added ligands, and reaction conditions are required for each case to optimize yields. Strickler, J. R.; Power, J. M, U.S. Pat. No. 5,847,175, issued 1998. Rohrmann, J.; Küber, F., U.S. Pat. No. 5,616,747, issued 1997. Fischer, D.; Schweier, G.; Brintzinger, H. H.; Damrau, H. R. H., Eur. Pat. Applic. 0 745 606 A2, 1996.

Ansa-metallocenes can also be prepared by amine elimination reactions of ansa-bis cyclopentadienes and metal amide complexes as discussed in U.S. Pat. No. 5,597,935. However, the amine elimination reaction produces amines such as $NMe_2H$ as byproducts which must be disposed of. Additionally, the amine elimination approach does not work well with some titanium or hafnium amides, crowded metal amides or crowded or weakly acidic cyclopentadienes. Some limitations of this method are described in Diamond, G. M.; Jordan, R. F., Petersen, J. L. *Organometallics* 1996, 15, 4030 and Christopher, J. N.; Jordan, R. F.; Petersen, J. L.; Young, V. G. Jr. *Organometallics* 1997, 16, 3044.

There is, therefore, a need for a process which would produce ansa-metallocene complexes, especially zirconocene complexes, in high yield. Additionally, there is a need for a process which will produce rac ansa-metallocenes in high yield without contamination by the meso isomer, since the rac isomer is most useful in stereoselective catalysis. The present invention fulfills these needs. These and other objectives, features, and advantages will become apparent after review of the following description and claims of the invention.

SUMMARY OF THE INVENTION

The invention is a process of preparing rac ansa-metallocene complexes in high yield by the reaction of a chelated bisamide group 4 metal complex, with an ansa-bis-cyclopentadienyl dianion reagent to yield a chelated bisamide metallocene compound, which may be converted to a metallocene dichloride, dialkyl, or other derivative in a subsequent step.

DETAILED DESCRIPTION OF THE PREFERRED EMBODIMENT

In the present invention, ansa-metallocene complexes of the general formula

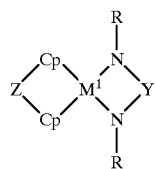

are prepared by the reaction of a chelated bisamide group 4 metal complex (I) with an ansa-bis-cyclopentadienyl reagent (II) as illustrated in equation 1.

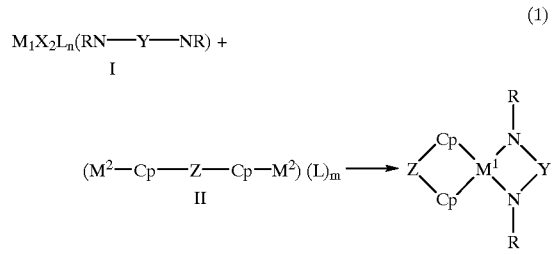

(1)

where M$^1$=Group 4 metal, Ti, Zr, Hf, preferably Zr;

X=a leaving group that can be displaced by a cyclopentadienyl ligand, e.g., halogen (F, Cl, Br, I), carboxylate, acetate, trifluoroacetate, diketonate, triflate, nitrate, etc., preferably chloride, the X groups may be the same or different or linked;

L=independently in each occurrence is a Lewis base, preferably selected from the group consisting of tetrahydrofuran (THF), Et$_2$O, amines, ethers, and pyridines;

n=a whole number from 0–4;

R=a hydrogen atom, a hydrocarbyl group having from 1 to 40 carbon atoms, or a silyl group, R may contain alkyl, aryl, silyl, haloalkyl, haloaryl, or halosilyl substituents, the two R groups can be the same or different, preferably phenyl;

Y=bridging group that links the two NR groups, preferably —CH$_2$CH$_2$CH$_2$—;

M$^2$=group 1 metal (Li, Na, K, Rb, Cs) or both M$^2$ together may be a single group 2 metal atom (Be, Mg, Ca, Sr, Ba);

Cp=independently and in each occurrence is a cyclopentadienyl, indenyl, fluorenyl, or related group that can Π-bond to the metal, or hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl, or related group;

Z=bridging or ansa group which links the Cp groups including, for example, silylene (—SiH$_2$—) or substituted silylene, benzo (C$_6$H$_4$) or substituted benzo, methylene (—CH$_2$—) or substituted methylene, ethylene (—CH$_2$CH$_2$—) or substituted ethylene bridges; and m=0–8.

Figure 1:
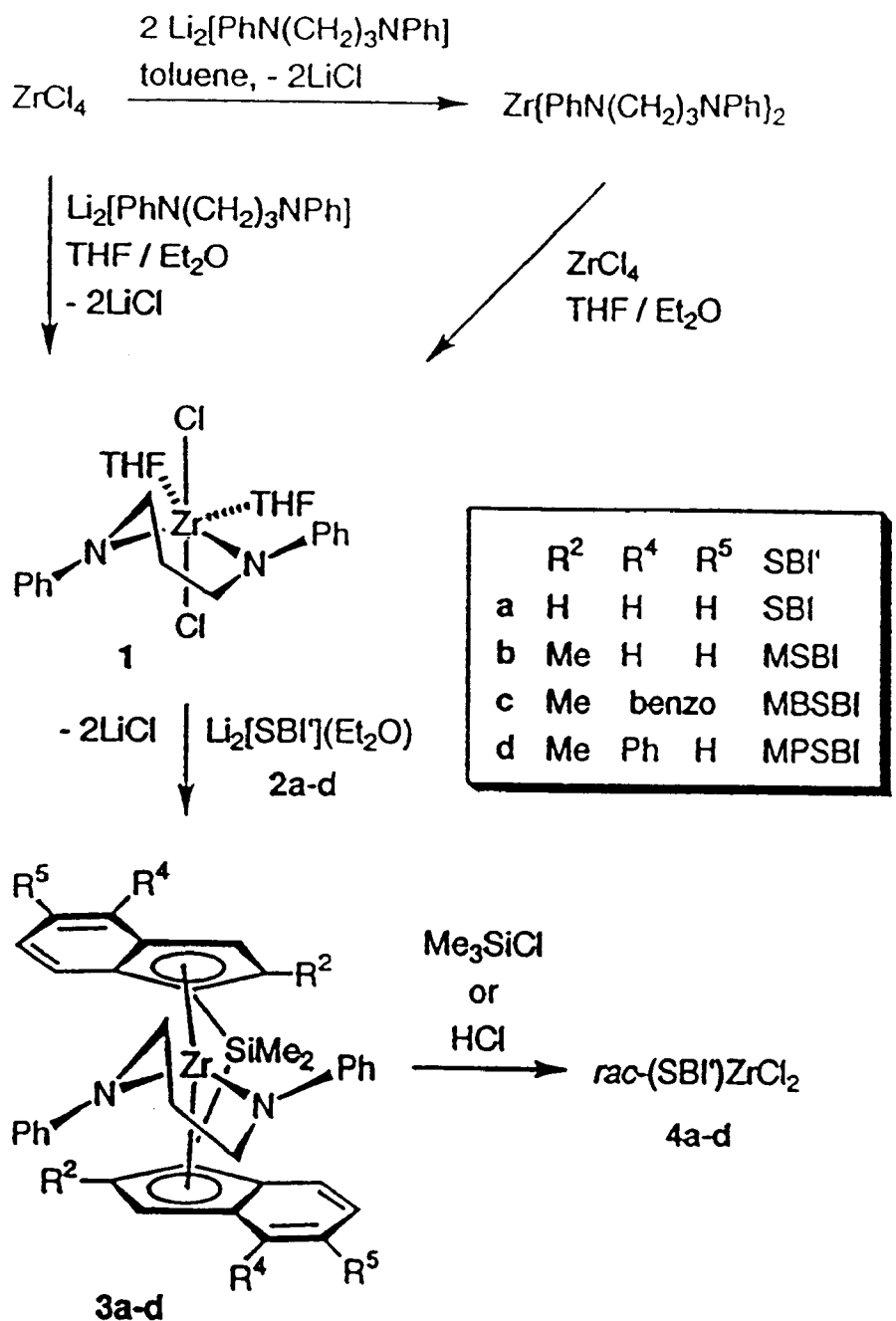
FIG. 1 is a schematic showing preparation of chelated bisamide complex Zr $(PhNCH_2CH_2CH_2NPh)$ $Cl_2$ $(THF)_2$ and subsequent conversions to rac ansa-zirconocene derivatives.

The starting materials in equation 1 may be prepared by known synthetic methods. The chelated bisamide group 4 metal complex M$^1$X$_2$L$_n$(RN—Y—NR) can be prepared by comproportionation reactions of homoleptic bisamide complexes M$^1$(RN—Y—NR)$_2$ and M$^1$X$_4$ compounds or by the reaction of M$^1$X$_4$ compounds with (RN—Y—NR)$^{2-}$ dianion reagents. For example, the chelated bisamide complex Zr(PhNCH$_2$CH$_2$CH$_2$NPh)Cl$_2$(THF)$_2$ (1) can prepared by two methods as shown in FIG. 1. The reaction of ZrCl$_4$ and two equivalents of Li$_2$[PhNCH$_2$CH$_2$CH$_2$NPh] in toluene affords Zr(PhNCH$_2$CH$_2$CH$_2$NPh)$_2$ as a yellow solid in 73% isolated yield. The comproportionation reaction of ZrCl$_4$ and Zr(PhNCH$_2$CH$_2$CH$_2$NPh)$_2$ in THF/Et$_2$O (1:1 by volume) yields 1 quantitatively. (This procedure is based on the method reported for the synthesis of Zr(NMe$_2$)$_2$Cl$_2$(THF)$_2$. Brenner, S.; Kempe, R.; Arndt, P. Z., Anorg. All. Chem. 1995, 621, 2021.) Alternatively, 1 can be prepared directly by the reaction of ZrCl$_4$ with one equivalent of Li$_2$[PhNCH$_2$CH$_2$CH$_2$NPh] in THF/Et$_2$O in 81% isolated yield.

The ansa-bis-cyclopentadienyl dianion reagent can be prepared by deprotonation of the corresponding ansa-bis-cyclopentadiene. For example, the lithium ansa-bis-cyclopentadienyl reagents Li$_2$[SBI'](Et$_2$O) (2a: SBI'=(1-indenyl)$_2$SiMe$_2$ (SBI); 2b: SBI'=(2-methyl-1-indenyl)$_2$SiMe$_2$ (MSBI); 2c: SBI'=(2-methyl-4,5-benz-1-indenyl)$_2$SiMe$_2$ (MBSBI); 2d: SBI'=(2-methyl-4-phenyl-1-indenyl)$_2$SiMe$_2$ (MPSBI)) can be prepared in 80–90% yield by reaction of the corresponding ansa-bis-cyclopentadienes with 2 equivalents of $^n$BuLi in Et$_2$O (23° C., 12 h).

The reaction between the chelated bisamide group 4 metal complex and the ansa-bis-cyclopentadienyl reagent can take place at any temperature from –80° C. to 200° C., but is preferably conducted in the range of 0° C. to 100° C., and most preferably at about 25° C. Typically the reaction is complete in less than 24 h. The reaction is desirably conducted in the presence of a nonaqueous, nonalcoholic solvent that at least partially dissolves one of the reactants. Typical of such solvents are hydrocarbons, such as benzene, toluene, hexane and heptane, and ethers, such as diethyl ether and tetrahydofuran. Preferably the solvent is diethyl ether. One may use an excess of the ansa-bis-cyclopentadienyl dianion reagent to increase the yield and rate of formation of the ansa-metallocene product. Preferably 1 to 1.3 equivalents of the ansa-bis-cyclopentadienyl dianion reagent are used per equivalent of the chelated bisamide group 4 metal complex I.

The structure and conformational properties of the chelated bisamide ligand (RN—Y—NR) of the chelated bisamide group 4 metal complex influence the yield and stereoselectivity of the ansa-metallocene products. In particular, the use of propane-bisamide ligands enables SiMe$_2$-bridged bis-indenyl zirconocene compounds to be prepared with high rac selectivity. For example, the reaction of 1 with 1 equivalent of the lithium ansa-bis-cyclopentadienyl reagents Li$_2$[SBI'](Et$_2$O) (2a:SBI'=(1-indenyl)$_2$SiMe$_2$ (SBI); 2b: SBI'=(2-methyl-1-indenyl)$_2$SiMe$_2$ (MSBI); 2c: SBI'=(2-methyl-4,5-benz-1-indenyl)$_2$SiMe$_2$ (MBSBI); 2d: SBI'=(2-methyl-4-phenyl-1-indenyl)$_2$SiMe$_2$ (MPSBI)) in Et$_2$O affords the corresponding rac-(SBI')Zr(PhNCH$_2$CH$_2$CH$_2$NPh) complexes 3a–3d in >90% NMR yield (FIG. 1). The $^1$H NMR spectra of 3a–3d each contain one SiMe$_2$ resonance, one 2-H or 2-Me resonance, three PhNCH$_2$CH$_2$CH$_2$NPh methylene resonances and appropriate aryl resonances consistent with C$_2$ symmetry. The meso isomers were not detected. Compounds 3c and 3d were isolated as red solids in 90% and 87% yield, respectively.

Figure 2:
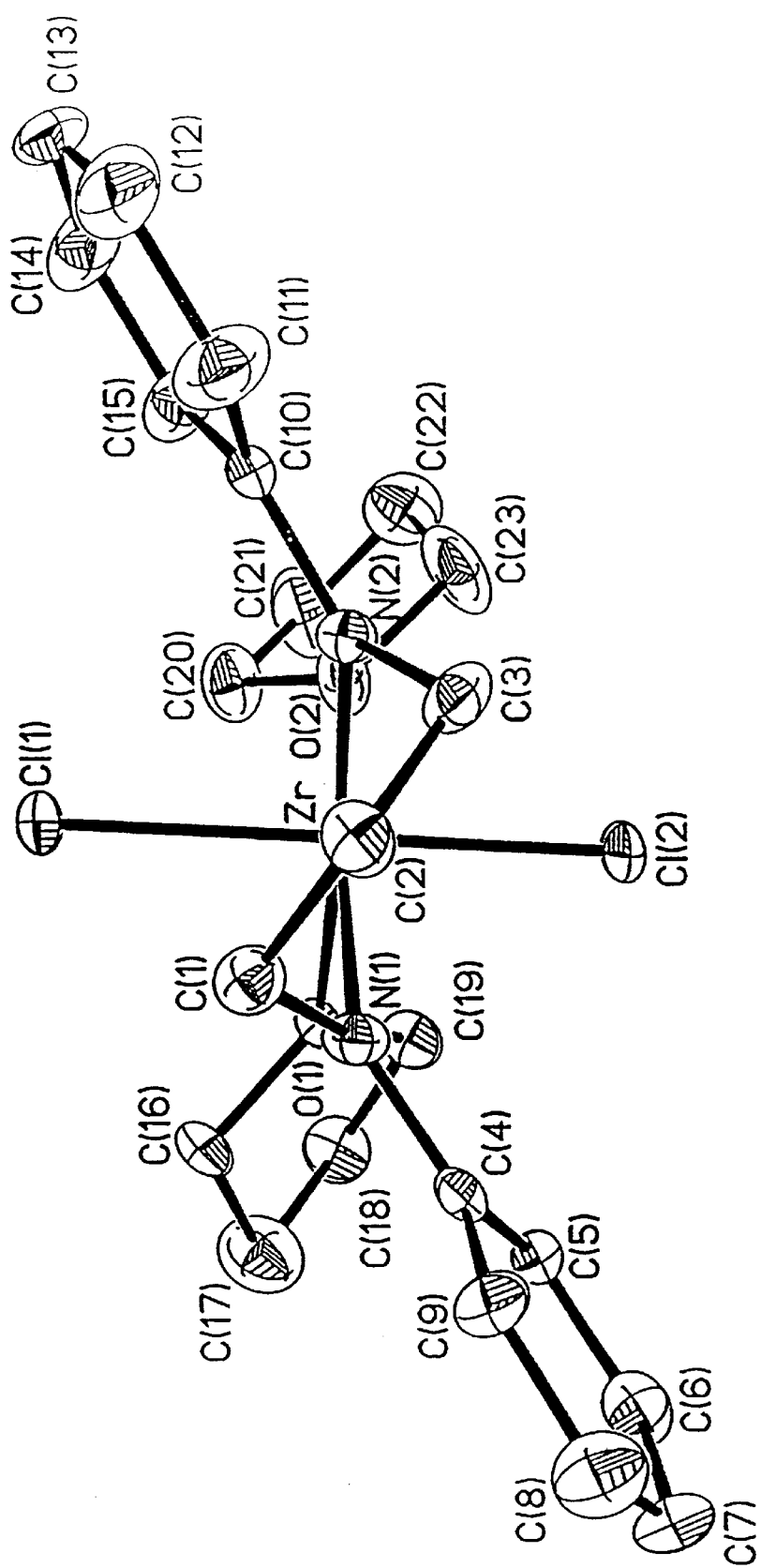
FIG. 2 shows the molecular structure of $Zr(PhNCH_2CH_2CH_2NPh)Cl_2(THF)_2$ (1). (Selected bond distances (Å) and angles (deg) not given in text: Zr-Cl(1) 2.4785(5), Zr—Cl(2) 2.4565(5), Cl(1)—Zr—Cl(2) 164.00(2), O(1)—Zr—O(2) 79.32(5).)
Figure 3:
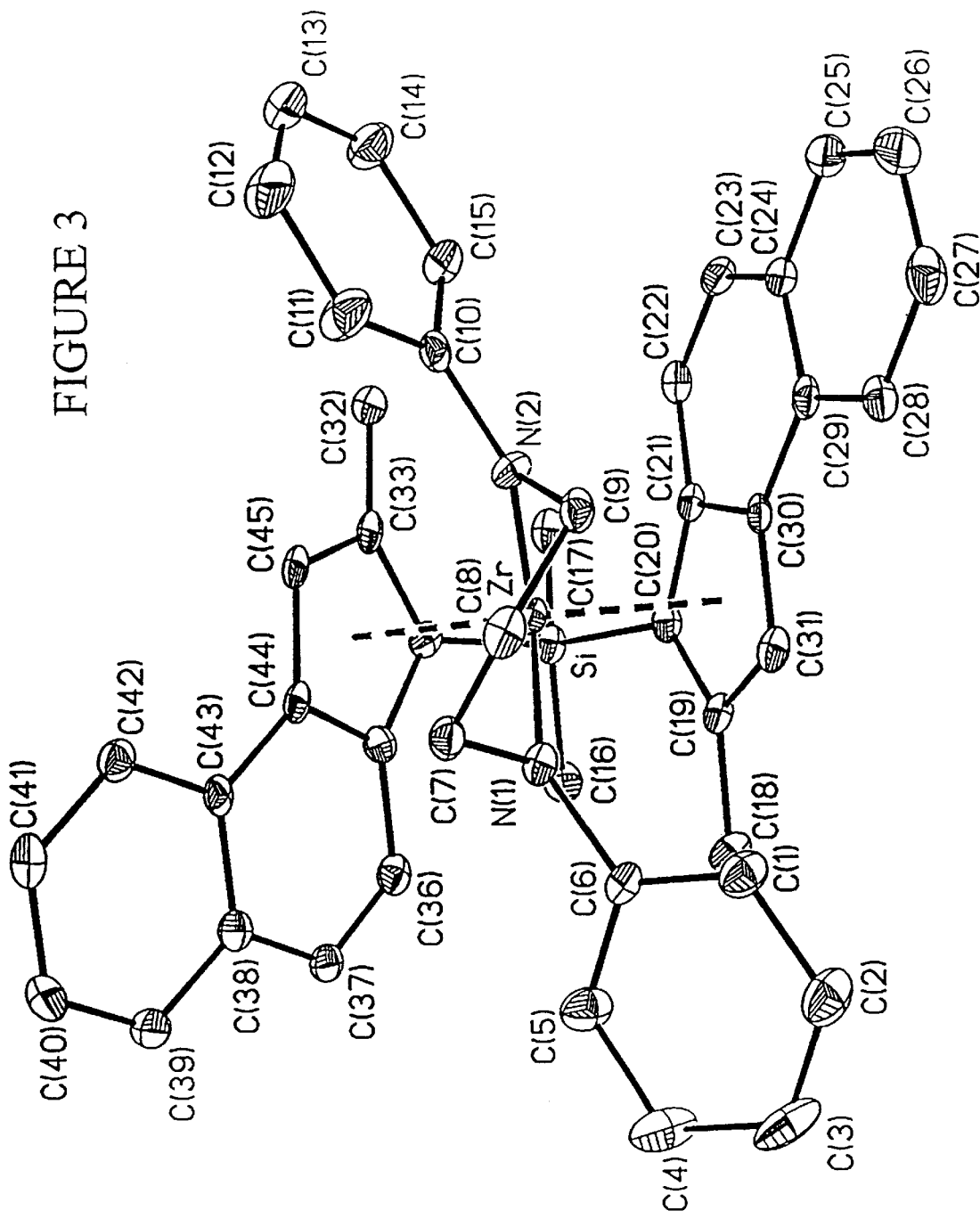
FIG. 3 shows a molecular structure of rac-(MBSBI)Zr(PhNCH$_2$CH$_2$CH$_2$NPh) (3c). (Selected bond distances (Å) not given in text: Zr—N(1) 2.073(2), Zr—N(2) 2.122(2).)

While not wishing to be bound by any theory, it is believed that the selectivity for rac metallocene products in FIG. 1 results from the fact that the favored twist conformation of the propane-bisamide ligand places the two N—Ph groups in an orientation that accommodates the rac-metallocene structure, but sterically disfavors the meso structure. The molecular structure of 1 in the solid state was established by X-ray crystallography and is shown in FIG. 2. Compound 1 is monomeric and has approximate $C_2$ symmetry with the $C_2$ axis lying along the Zr—C(2) vector. The geometry at Zr is distorted octahedral and the weak donor THF ligands are trans to the strong donor amide groups. The Zr—N bond distances (2.082(2), 2.080(2) Å) are normal and the N(1)—Zr—N(2) angle (91.63(6)°) is close to the ideal octahedral value. The 6-membered C(1)—N(1)—Zr—N(2)—C(3)—C(2) chelate ring adopts a twist conformation. The N(1), Zr, N(2) and C(2) atoms are coplanar to within 0.02 Å, and C(1) and C(3) lie 0.79 Å above and below the N(1)—Zr—N(2)—C(2) plane, respectively. This conformation places the two phenyl rings on opposite sides of the N(1)—Zr—N(2)—C(2) plane (C(4)—N(1)—N(2)—C(10) torsion angle 145.2°). The molecular structure of (MBSBI)Zr(PhNCH$_2$CH$_2$CH$_2$NPh) (3c) in the solid state was also determined by X-ray crystallography and is shown in FIG. 3. The Zr-bisamide unit in 3c is structurally very similar to that in 1. The twist conformation of the chelate ring, the large C(6)—N(1)—N(2)—C(10) torsion angle (142.8°) and the N(1)—Zr—N(2) angle (86.77 (9)°) are very similar to the corresponding features in 1.

For comparison, the reaction of Li$_2$[MBSBI](OEt$_2$) (2c) with Zr(NMePh)$_2$Cl$_2$(THF)$_2$, the non-chelated analogue of 1, yields a 1/1 mixture of rac and meso-(MBSBI)Zr(NMePh)$_2$ along with 20% of the dinuclear species (MBSBI){Zr(NMePh)$_2$Cl}$_2$. In this case, meso-(MBSBI)Zr(NMePh)$_2$ is accessible because rotation around the Zr—NMePh bond on the crowded side of the metallocene unit relieves steric crowding between the N-phenyl ring and indenyl groups. Additionally, the reaction of 2c with the ethane-bisamide complex {Zr(PhNCH$_2$CH$_2$NPh)Cl$_2$(THF)}$_2$ yields a 2/1 mixture of rac and meso-(MBSBI)Zr(PhNCH$_2$CH$_2$NPh). The 5-membered ZrNCH$_2$CH$_2$N chelate rings in rac and meso-(MBSBI)Zr(PhNCH$_2$CH$_2$NPh) adopt envelope conformations in which the one N—Ph group lies in the N—Zr—N plane, which allows the meso isomer to form.

It is believed that the metallocene bisamide complexes produced by equation 1 may, when activated by a suitable cocatalyst, be used as catalysts in many applications. Alternatively, the metallocene bisamide complexes produced in equation 1 may be converted to the more commonly used derivatives, such as metallocene dichloride or dialkyl complexes. The metallocene dichloride derivatives can be synthesized by synthesis of chelated bis-amide metallocenes by equation 1 followed by conversion of these products to dichloride derivatives by equation 2 or 3.

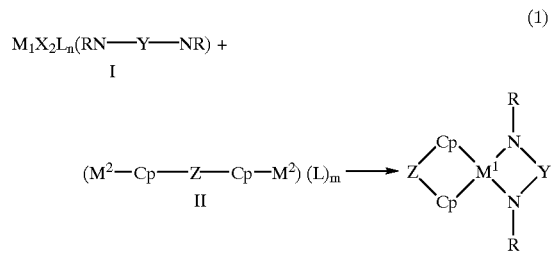

(1)

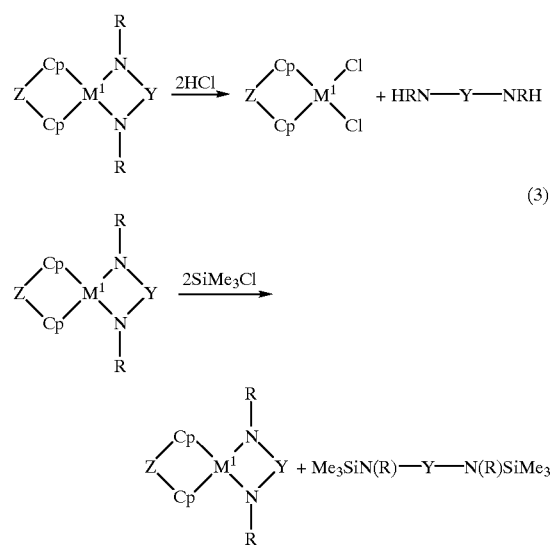

where $M^1$=Group 4 metal, Ti, Zr, Hf, preferably Zr;

X=a leaving group that can be displaced by a cyclopentadienyl ligand, e.g., halogen (F, Cl, Br, I), carboxylate, acetate, trifluoroacetate, diketonate, triflate, nitrate, etc., preferably chloride, the X groups may be the same or different or linked;

L=independently in each occurrence is a Lewis base, preferably selected from the group consisting of tetrahydrofuran (THF), Et$_2$O, amines, ethers and pyridines;

n=a whole number from 0–4;

R=a hydrogen atom, a hydrocarbyl group having from 1 to 40 carbon atoms, or a silyl group, R may contain alkyl, aryl, silyl, haloalkyl, haloaryl, or halosilyl substituents, the two R groups can be the same or different, preferably phenyl;

Y=bridging group that links the two NR groups, preferably —CH$_2$CH$_2$CH$_2$—;

$M^2$=group 1 metal (Li, Na, K, Rb, Cs) or both $M^2$ together may be a single group 2 metal atom (Be, Mg, Ca, Sr, Ba);

Cp=independently and in each occurrence is a cyclopentadienyl, indenyl, fluorenyl, or related group that can Π-bond to the metal, or hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl, or related group;

Z=bridging or ansa group which links the Cp groups including, for example, silylene (—SiH$_2$—) or substituted silylene, benzo (C$_6$H$_4$) or substituted benzo, methylene (—CH$_2$—) or substituted methylene, ethylene (—CH$_2$CH$_2$—) or substituted ethylene bridges; and m=0–8.

Trimethylsilyl chloride (SiMe$_3$Cl) is an effective reagent for the conversion of uncrowded chelated bis-amide metallocenes to metallocene dichlorides, while HCl can be used for crowded cases. For example, 3a is cleanly converted to 4a (100% NMR) by reaction with Me$_3$SiCl in CD$_2$Cl$_2$ at 60° C. (sealed tube, FIG. 1). In contrast, no reaction is observed between 3d and Me$_3$SiCl in CH$_2$Cl$_2$ (100° C., 30 h, sealed tube). However 3b–d react cleanly with HCl in Et$_2$O or toluene at −78° C. to afford the corresponding rac zirconocene dichlorides 4b–d (FIG. 1). Rac-(MBSBI)ZrCl$_2$ (4c) was isolated in 70% yield (based on 1) by initial generation of 3c from 1 and 2c, filtration to remove the LiCl coproduct, treatment with HCl at −78° C., removal of the solvent and washing with benzene to remove the PhNHCH$_2$CH$_2$CH$_2$NHPh coproduct. Dichlorides 4b and 4d were isolated in 76% and 51% yield, respectively, (based on ZrCl$_4$) by in situ generation of 1 from ZrCl$_4$ and Li$_2$[PhNCH$_2$CH$_2$CH$_2$NPh], treatment with the appropriate Li$_2$[SBI'](Et$_2$O) reagent, filtration to remove the LiCl coproduct, treatment with HCl at −78° C. and filtration. The lower isolated yield for 4d is due to its high solubility.

It is not necessary to isolate the chelated-bis-amide metallocene intermediates. They can be generated and then directly converted to derivatives. The (Cp—Z—Cp)M$^1$(NR—Y—NR) compounds could be converted to many other derivatives using standard chemistry, for example, reaction with AlMe$_3$ would likely give (Cp—Z—Cp)M$^1$Me$_2$ compounds.

The following examples are offered to further illustrate but not limit the process of the present invention.

EXAMPLES

Synthetic Procedures and Characterization for New Compounds

All manipulations were carried out under purified nitrogen in a Vacuum Atmospheres glovebox or on a high vacuum line. Toluene, tetrahydrofuran, benzene, and ether were distilled under nitrogen from sodium/benzophenone ketyl. CH$_2$Cl$_2$ was distilled under nitrogen from P$_2$O$_5$. ZrCl$_4$ was purchased from CERAC and sublimed. N-methylaniline and N,N'-diphenylethanediamine (PhNHCH$_2$CH$_2$NHPh) were purchased from Aldrich (Milwaukee, Wis.) and used as received. N,N'-diphenylpropanediamine (PhNHCH$_2$CH$_2$CH$_2$NHPh) was prepared by a literature procedure (Billman, J. J.; Caswell, L. R. *Synthesis* (1951), 1041.). The bis-indenes (1-indenyl)$_2$SiMe$_2$ (Christopher, J. N.; Diamond, G. M.; Jordan, R. F.; Petersen, J. L. *Organometallics* (1996), 15, 4038. Marechal, E.; Tortal, J., *P.C.R. Acad. Sci. Paris,* 1968, 267, 467. Sommer, L. H.; Marans, N. S., *J. Am. Chem. Soc.,* 1951, 73, 5135.), (2-Me-1-indenyl)$_2$SiMe$_2$ (Spaleck, W.; Küber, F.; Winter, A.; Rohrmann, J.; Bachmann, B.; Antberg, M.; Dolle, V.; Paulus, E. F., *Organometallics,* 1994, 13, 954), (2-Me-4,5-benz-1-indenyl)$_2$SiMe$_2$ (Stehling, U.; Diebold, J.; Kirsten, R.; Röll, W.; Brintzinger, H. H.; Jüngling, S.; Mülhaupt, R.; Langhauser, F., *Organometallics,* 1994, 13, 964), and (2-Me-4-Ph-1-indenyl)$_2$SiMe$_2$ (Spaleck, W.; Küber, F.; Winter, A.; Rohrmann, J.; Bachmann, B.; Antberg, M.; Dolle, V.; Paulus, E. F., *Organometallics,* 1994, 13, 954) were prepared by literature methods and converted to the corresponding Li$_2$[SBI'](Et$_2$O) salts 2a–d in 80–90% yield by reaction with $^n$BuLi in Et$_2$O (2 equiv, 23° C., overnight in Et$_2$O); 2a–d were isolated by filtration, washed with hexane and dried under vacuum. NMR spectra were recorded on a Bruker AMX-360 spectrometer, in sealed or Teflon-valved tubes at ambient probe temperature (23° C.) unless otherwise indicated. $^1$H and $^{13}$C NMR chemical shifts are reported versus Me$_4$Si and were determined by reference to the residual solvent peaks. Coupling constants are given in Hz. Elemental analyses were performed by Desert Analytics Laboratory (Tucson, Ariz.).

Example 1

Synthesis of Li$_2$[PhNCH$_2$CH$_2$CH$_2$NPh]

A solution of $^n$BuLi in hexanes (32 mL, 1.6 M, 51.2 mmol) was added to a solution of PhNHCH$_2$CH$_2$CH$_2$NPh (5.18 g, 22.9 mmol) in benzene (70 mL) over 10 min. by syringe at 23° C. The resulting slurry was stirred for 24 h and filtered. The white solid was washed with benzene (20 mL) and dried under vacuum (5.02 g, 93%). $^1$H NMR (THF-d8): δ 6.76 (t, J=8, 4H, Ph), 6.28 (d, J=8, 4H, Ph), 5.92 (t, J=8, 2H, Ph), 3.04 (t, J=4, 4H, NCH$_2$), 1.94 (quint, J=4, 2H, CH$_2$)

Example 2

Synthesis of Zr(PhNCH$_2$CH$_2$CH$_2$NPh)$_2$

ZrCl$_4$ (1.23 g, 5.29 mmol) was added to an off-white slurry of Li$_2$[PhNCH$_2$CH$_2$CH$_2$NPh] (2.52 g, 10.6 mmol) in toluene (70 mL) in several portions over 2 h at 23° C. The mixture was stirred at 23° C. for 46 h and THF (35 mL) was added. The stirring was continued for 1.5 h. The volatiles were removed under vacuum and benzene (50 mL) was added to the resulting solid. The mixture was stirred for 30 min. and filtered. The yellow solid was washed with benzene (10 mL). The filtrate and wash were combined. The volatiles were removed under vacuum affording a yellow solid which was washed with pentane (50 mL) and dried under vacuum (2.10 g, 73%). Anal. Calcd for C$_{30}$H$_{32}$N$_4$Zr: C, 66.74; H, 5.99; N, 10.38. Found: C, 66.93; H, 6.12; N, 10.08. $^1$H NMR (THF-d$_8$): δ 7.04 (t, J=8, 4H, m-Ph), 6.78 (d, J=8, 4H, o-Ph), 6.63 (t, J=8, 2H, p-Ph), 3.68 (t, J=5, 4H, CH$_2$), 2.29 (quint, J=5, 2H, CH2)

Example 3

Synthesis of Zr(PhNCH$_2$CH$_2$CH$_2$NPh)Cl$_2$(THF)$_2$ (1)

Method A: A flask was charged with Zr(PhNCH$_2$CH$_2$CH$_2$NPh)$_2$ (1.10 g, 2.04 mmol) and ZrCl$_4$ (0.476 g, 2.04 mmol), and THF (30 mL) and Et$_2$O (30 mL) were added at 0° C. The resulting clear yellow solution was stirred for 16 h at 23° C., concentrated to ca. 10 mL and cooled to −20° C. for 23 h. No solid formed. The volatiles were removed under vacuum at 23° C. to yield a yellow solid (1.77 g, 100%). Anal. Calcd for C$_{23}$H$_{32}$Cl$_2$N$_2$O$_2$Zr: C, 52.05; H, 6.09; N, 5.28. Found: C, 51.79; H, 6.21; N, 5.19. $^1$H NMR (THF-d8, 23° C.): δ 7.45 (d, J=8, 4H, Ph), 7.20 (t, J=8, 4H, Ph), 6.83 (t, J=8, 2H, Ph), 4.03 (t, J =6, 4H, CH$_2$N), 3.71 (br, 4H, THF), 2.00 (m, 2H, CH$_2$), 1.88 (m, 4H, THF).

Method B: A flask was charged with ZrCl$_4$ (0.718 g, 3.08 mmol) and Li$_2$[PhNCH$_2$CH$_2$CH$_2$NPh] (0.734 g, 3.08 mmol), and THF (25 mL) and Et$_2$O (25 mL) were added at 0° C. The mixture was stirred for 9 h at 23° C. The volatiles were removed under vacuum affording a yellow solid. Benzene (60 mL) was added and the mixture was stirred for 1 h and filtered. The volatiles were removed from the filtrate under vacuum to afford a yellow solid which was identified as Zr(PhNCH$_2$CH$_2$CH$_2$NPh)Cl$_2$(THF)$_2$ by $^1$H NMR (isolated yield 1.32 g, 81%). Compound 1 was characterized by single crystal X-ray diffraction. Single crystals of 1 for X-ray diffraction were obtained by slow diffusion of hexanes into benzene solution over several weeks. X-ray data for 1: tetragonal, P4$_2$/n, a=b=24.977(1) Å, c=7.8479(4) Å, V=4895.8(4) Å3, Z =8, T=173(2) K, D$_{calc}$=1.440 g/cm$^3$; R1=0.0248, wR2=0.0708 for I>2σ(I); GOF on F$^2$=0.997. The molecular structure of 1 is shown in FIG. 2.

Example 4

Generation of Rac-(MSBI)Zr (PhNCH$_2$CH$_2$CH$_2$NPh) (3b)

A flask was charged with Zr(PhNCH$_2$CH$_2$CH$_2$NPh)Cl$_2$(THF)$_2$ (0.045 g, 0.079 mmol) and Li$_2$[MSBI](Et$_2$O) (0.043 g, 0.079 mmol). Et$_2$O (2 mL) was added by vacuum transfer. The mixture was stirred for 17 h at 23° C. The volatiles were removed under vacuum and C$_6$D$_6$ (2 mL) was added. A portion of the mixture (ca. 1 mL) was transferred to a resealable NMR tube. The $^1$H NMR spectrum established that complete conversion to rac-(MSBI)Zr (PhNCH$_2$CH$_2$CH$_2$NPh) had occurred. $^1$H NMR (C$_6$D$_6$) δ 7.74 (d, J=7, 2H, indenyl), 7.23 (m, 6H, indenyl and Ph), 6.96 (m, 4H), 6.72 (m, 2H), 6.55 (d, J=7, 4H), 6.2 (s, 2H, indenyl), 3.60 (dt, J=14, 7, 2H, CH$_2$), 3.03 (td, J=11, 4, 2H, CH$_2$), 2.01 (s, 6H, 2-Me), 1.24 (m, 2H, CH$_2$), 0.88 (s, 6H, SiMe$_2$).

Example 5

Synthesis of Rac-(MBSBI)Zr (PhNCH$_2$CH$_2$CH$_2$NPh) (3c)

A flask was charged with Zr(PhNCH$_2$CH$_2$CH$_2$NPh)Cl$_2$ (THF)$_2$ (0.567 g, 1.00 mmol) and Li$_2$[MBSBI](Et$_2$O) (0.511 g, 1.00 mmol), and Et$_2$O (50 mL) was added by vacuum transfer. The mixture was stirred for 18 h at 23° C. The volatiles were removed under vacuum. The resulting solid was taken up in benzene (50 mL) and filtered. The volatiles were removed from the filtrate under vacuum affording a red solid (0.75 g). The $^1$H NMR of this crude product showed that no meso-(MBSBI)Zr(PhNCH$_2$CH$_2$CH$_2$NPh) was present. This material was recrystallized from toluene/hexane (1:10 by volume) at −20° C. to yield rac-(MBSBI)Zr(PhNCH$_2$CH$_2$CH$_2$NPh) (0.68 g, 90%). Anal. Calcd for C$_{45}$H$_{42}$N$_2$SiZr: C, 73.74; H, 5.81; N, 3.83. Found: C, 73.82; H, 5.92; N, 3.34. $^1$H NMR (C$_6$D$_6$): δ 7.89 (d, J=7.2, 2H, indenyl), (7.82 (d, J=7.2, 2H, indenyl), 7.52 (m, 2H), 7.33 (d, J=7.2, 2H, indenyl), 7.20 (t, J=7.2, 4H), 7.13 (m, 4H), 6.95 (t, J=7.2, 2H), 6.72 (s, 2H), 6.59 (d, J=7.2, 4H), 3.45 (dt, J=14, 7.2, 2H, CH$_2$), 2.18 (s, 6H, 2-Me), 2.12 (dt, J=14, 3.6, 2H, CH$_2$), 0.99 (s, 6H, SiMe$_2$), 0.89 (br s, 2H, CH$_2$). Compound 3c was characterized by single crystal X-ray diffraction. Single crystals for X-ray diffraction were obtained by crystallization from benzene. X-ray data for 3c: triclinic, P1 bar, a=10.3355(6) Å, b=12.1037(7) Å, c=14.8777(8) Å, α=93.503(1)°, ⊕=97.219(1)°, γ=107.125(1)°, V=1755.1(2) Å$^3$, Z=2, T=173(2) K, D$_{calc}$=1.382 g/cm$^3$; R1=0.0453, wR2=0.0751 for I>2σ(I); GOF on F$^2$=1.010.

Example 6

Synthesis of Rac-(MPSBI)Zr (PhNCH$_2$CH$_2$CH$_2$NPh) (3d)

A flask was charged with Zr(PhNCH$_2$CH$_2$CH$_2$NPh)Cl$_2$ (THF)$_2$ (0.522 g, 0.929 mmol) and Li$_2$[MPSBI](Et$_2$O) (0.506 g, 0.922 mmol) and Et$_2$O (70 mL) was added by vacuum transfer. The mixture was stirred for 19 h at 23° C. The volatiles were removed under vacuum to yield a red solid. The solid was taken up in benzene (50 mL) and filtered. The volatiles were removed from the filtrate under vacuum to afford a red solid. Pentane (15 mL) was added to the solid and the mixture was stirred for 20 min and filtered. The red solid was taken up in benzene (35 mL) and filtered. The volatiles were removed from the filtrate under vacuum to afford rac-(MPSBI)Zr(PhNCH$_2$CH$_2$CH$_2$NPh) (0.63 g, 87%) as a red solid. A portion of this solid (100 mg) was dissolved in benzene (3 mL) and precipitated out by addition of hexanes (10 mL). The resulting solid was collected and dried under vacumm (71 mg). Anal. Calcd for C$_{49}$H$_{46}$N$_2$SiZr: C, 75.19; H, 5.94; N, 3.58. Found: C, 74.41; H, 6.23; N, 3.11. $^1$H NMR (C$_6$D$_6$); δ=7.92 (d, J=7.2, 2H, indenyl), 7.49 (d, J=7.2, 4H, indenyl), 7.36–7.25 (m, 8H), 7.07 (m, 6H), 6.87 (t, J=7.2, 2H), 6.45 (s, 2H), 6.18 (d, J=7.2, 4H), 3.15 (m, 2H, CH$_2$), 2.57 (m, 2H, CH$_2$), 2.11 (s, 6H, 2-Me), 1.25 (s, 6H, SiMe$_2$), 0.78 (br s, 2H, CH$_2$). $^{13}$C{$^1$H} NMR (CD$_2$Cl$_2$, 23° C.): 161.8, 140.9, 137.5, 132.4, 128.6, 129.0, 128.1, 127.6, 124.8, 124.5, 124.0, 123.7, 121.8, 116.0, 93.2, 59.5, 21.5, 19.0, 2.6 (two aromatic peaks may be obscured by the solvent).

Example 7

Generation of rac-(SBI)ZrCl$_2$ (4a)

A flask was charged with Zr(PhNCH$_2$CH$_2$CH2NPh)Cl$_2$ (THF)$_2$ (0.045 g, 0.079 mmol) and Li$_2$[SBI](Et$_2$O) (0.030 g, 0.080 mmol), and Et$_2$O (2 mL) was added by vacuum transfer. The mixture was stirred for 15 h at 23° C. The volatiles were removed under vacuum and C$_6$D$_6$ (2 mL) was added. A portion of the mixture (1 mL) was transferred to a resealable NMR tube. The $^1$H NMR spectrum established that complete conversion to rac-(SBI)Zr (PhNCH$_2$CH$_2$CH$_2$NPh) (3a) had occurred. $^1$NMR (C$_6$D$_6$) δ 7.58 (d, J=8, 2H, indenyl), 7.26 (t, J=7, 2H, indenyl), 6.97 (d, J=8, 2H, indenyl), 6.88 (t, J=7, 2H, indenyl), 6.78 (t, J=8, 2H, indenyl), 6.52 (m, 4H, Ph), 6.45 (d, 4H, J=8, Ph), 6.37 (d, J=2, Ph), 3.18 (dt, J=13, 2, 2H, CH$_2$), 3.03 (quint, J=6, 2H, CH$_2$), 1.38 (m, 2H, CH$_2$), 0.80 (s, 6H, SiMe$_2$). The volatiles were removed from the NMR tube under vacuum and Me$_3$SiCl (0.051 g, 0.469 mmol) and CD$_2$Cl$_2$ (0.6 mL) were added. The tube was heated to 60° C. for 11 h and the color changed from red to yellow. The $^1$H NMR spectrum established that complete conversion to rac-(SBI)ZrCl$_2$ had occurred; no meso-(SBI)ZrCl$_2$ was detected. Herrmann, W. A.; Rohrmann, J.; Herdtweck, E.; Spaleck, W.; Winter, A., *Angew. Chem., Int. Ed. Engl.*, 1989, 28, 1511. $^1$H NMR (CD$_2$Cl$_2$): δ 7.57 (m, 4H, indenyl), 7.38 (m, 2H, indenyl), 7.13 (m, 2H, indenyl), 6.91 (d, J=3, 2H, indenyl), 6.14 (d, J=3, 2H, indenyl), 1.15 (s, 6H, SiMe$_2$)

Example 8

Synthesis of Rac-(MSBI)ZrCl$_2$ (4b)

Method A: A flask was charged with Zr(PhNCH$_2$CH$_2$CH$_2$NPh)Cl$_2$(THF)$_2$ (0.585 g, 1.10 mmol) and Li$_2$[MSBI](Et$_2$O) (0.444 g, 1.10 mmol), and Et$_2$O (50 mL) was added by vacuum transfer. The mixture was stirred for 22 h at 23° C. The volatiles were removed under vacuum. The resulting solid was taken up in benzene (40 mL) and filtered. The volatiles were removed from the filtrate under vacuum to afford a red solid. The solid was taken up in benzene (30 mL) and filtered. The volatiles were removed from the filtrate under vacuum to afford a red solid (0.638 g). A portion of the solid (0.334 g) was dissolved in CH$_2$Cl$_2$/Et$_2$O (30 mL, 1:1 by volume). The solution was cooled to −78° C. and HCl (1.0 mL of a 1.0 M solution in Et$_2$O, 1.0 mmol) was added. The mixture was stirred for 10 min at −78° C. The red solution turned into a yellow-orange slurry. The volatiles were removed under vacuum. The yellow-orange solid was washed with hexanes (20 mL) and benzene (2×10 mL) and dried under vacuum (yield 0.18 g, 73%).

Method B: A flask was charged with ZrCl$_4$ (1.27 g, 5.45 mmol) and Li$_2$[PhNCH$_2$CH$_2$CH$_2$NPh] (1.30 g, 5.46 mmol), and THF (40 mL) and Et$_2$O (40 mL) were added at 23° C. The mixture was stirred for 32 h at 23° C. The volatiles were removed under vacuum affording a yellow oily solid. Benzene (10 mL) was added and the mixture was stirred for 10 min. The volatiles were removed under vacuum yielding a yellow solid. Li$_2$[MSBI](Et$_2$O) (2.20 g, 5.45 mmol) and Et₂O (60 mL) were added. The mixture was stirred for 17 h at 23° C. The volatiles were removed under vacuum. Toluene (50 mL) was added and the resulting slurry was stirred for 2 h and filtered to remove LiCl. The red filtrate was cooled to −78° C. and HCl (12 mL of 1.0 M solution in Et₂O, 12 mmol) was added at −78° C. The mixture was stirred for 1 h at −78° C. and warmed to 23° C. The resulting yellow-orange slurry was stirred for 20 min at 23° C. The mixture was cooled to −78° C. and filtered. The yellow-orange solid was collected and dried under vacuum (yield 2.05 g, 76% based on ZrCl₄). The ¹H NMR spectrum established that the yellow orange solid was pure rac-(MSBI)ZrCl₂. Spaleck, W.; Antberg, M.; Rohrmann, J.; Winter, A.; Bachmann, B.; Kiprof. P.; Behm, J.; Herrmann, W. A. *Angew. Chem., Int. Ed. Engl.*, 1992, 31, 1347. Anal. Calcd for C₂₂H₂₂Cl₂SiZr: C, 55.43; H, 4.66. Found: C, 54.93; H, 4.65. ¹H NMR (CD₂Cl₂): δ 7.68 (dd, J=8, 1, 2H, indenyl) 7.48 (dt, J=8, 1, 2H, indenyl), 7.35 (m, 2H, indenyl), 7.01 (m, 2H, indenyl), 6.78 (s, 2H, indenyl), 2.21 (s, 6H, 2-Me), 1.30 (s, 6H, SiMe₂).

Example 9

Synthesis of Rac-(MBSBI)ZrCl₂ (4c)

A flask was charged with Zr(PhNCH₂CH₂CH₂NPh)Cl₂(THF)₂ (0.548 g, 1.03 mmol) and Li₂[MBSBI](Et₂O) (0.528 g, 1.03 mmol), and Et₂O (40 mL) was added by vacuum transfer. The mixture was stirred for 19 h at 23° C. The volatiles were removed under vacuum and the resulting red solid was heated at 45° C. for 5 h under vacuum. The solid was taken up in benzene (40 mL), stirred for 20 min and filtered. The volatiles were removed from red filtrate under vacuum. Et₂O (30 mL) was added and the flask was cooled to −78° C. HCl (2.2 mL of 1.0 M solution in Et₂O, 2.2 mmol) was added to the mixture at −78° C. The mixture was stirred for 50 min at −78° C. and the color changed from red to yellow. The volatiles were removed under vacuum at 23° C. The resulting yellow solid was washed with benzene (40 mL) and dried under vacuum (0.415 g, 70%). The ¹H NMR spectrum established that the yellow solid was pure rac-(MBSBI)ZrCl₂. Spaleck, W.; Küber, F.; Winter, A.; Rohrmann, J.; Bachmann, B.; Antberg, M.; Dolle, V.; Paulus, E. F., *Organometallics*, 1994, 13, 954. ¹H NMR (CD₂Cl₂): δ 7.95 (m, 2H, indenyl), 7.79 (m, 2H, indenyl), 7.63 (d, J=11, 2H, indenyl), 7.55 (m, 4H, indenyl), 7.37 (d, J=11, 2H, indenyl), 7.26 (s, 2H, indenyl), 2.35 (s, 6H, 2-Me), 1.35 (s, 6H, SiMe₂).

Example 10

Synthesis of Rac-(MPSBI)ZrCl₂ (4d)

Method A: A flask was charged with Zr(PhNCH₂CH₂CH₂NPh)Cl₂(THF)₂ (0.351 g, 0.661 mmol) and Li₂[MPSBI](Et₂O) (0.367 g, 0.661 mmol), and Et₂O (50 mL) was added by vacuum transfer. The mixture was stirred for 21 h at 23° C. The volatiles were removed under vacuum. The resulting solid was taken up in benzene (40 mL) and filtered. The volatiles were removed from the filtrate under vacuum to afford a red solid. The solid was taken up in benzene (30 mL) and filtered. The volatiles were removed from the filtrate under vacuum to yield a red solid (0.464 g). A portion of the solid (0.277 g) was dissolved in CH₂Cl₂/Et₂O (30 mL, 1:1 by volume). The solution was cooled to −78° C. and HCl (0.70 mL of 1.0 M solution in Et₂O, 0.70 mmol) was added. The mixture was stirred for 10 min at −78° C. The red solution turned into a yellow slurry and the volatiles were removed under vacuum. The yellow solid was washed with with hexanes (2×20 mL) and dried under vacuum (0.200 g). The ¹H NMR spectrum established that this product was a mixture of rac-(MPSBI)ZrCl₂ and PhNHCH₂CH₂CH₂NHPh. The solid was washed with benzene (10 mL) to afford pure rac-(MPSBI)ZrCl₂ (0.103 g, 45%).

Method B: A flask was charged with ZrCl₄ (0.776 g, 3.33 mmol) and Li₂[PhNCH₂CH₂CH₂NPh] (0.793 g, 3.33 mmol), and THF (35 mL) and Et₂O (35 mL) were added by vacuum transfer. The mixture was stirred for 32 h at 23° C. The volatiles were removed under vacuum affording a yellow, oily solid. Benzene (10 mL) was added and the mixture was stirred for 10 min. The volatiles were removed under vacuum yielding a yellow solid. Li₂[MPSBI](Et₂O) (1.90 g, 3.33 mmol) and Et₂O (60 mL) were added. The mixture was stirred for 17 h at 23° C. The volatiles were removed under vacuum. Toluene (60 mL) was added and the resulting slurry was stirred for 2 h and filtered. The red filtrate was cooled to −78° C. and HCl (7.3 mL of 1.0 M solution in Et₂O, 7.3 mmol) was added at −78° C. The mixture was stirred for 1 h at −78° C. and warmed to 23° C. The resulting yellow slurry was stirred for 20 min at 23° C. The mixture was cooled to −78° C. and filtered. The yellow solid was collected and dried under vacuum (1.10 g, 51% vs. ZrCl₄). The ¹H NMR spectrum established that the yellow solid was pure rac-(MPSBI)ZrCl₂. Spaleck, W.; Küber, F.; Winter, A.; Rohrmann, J.; Bachmann, B.; Antberg, M.; Dolle, V.; Paulus, E. F., *Organometallics*, 1994, 13, 954. ¹H NMR (CD₂Cl₂): δ 7.70 (m, 2H, indenyl), 7.62 (m, 4H, indenyl) 7.43 (m, 4H, indenyl), 7.36 (m, 4H, indenyl), 7.13 (m, 2H, indenyl), 6.92 (s, 2H, indenyl), 2.25 (s, 6H, 2-Me), 1.36 (s, 6H, SiMe₂).

Example 11

Synthesis of Zr(NMePh)₄

ZrCl₄ (2.20 g, 9.44 mmol) was added to an off-white slurry of LiNMePh (4.26 g, 37.7 mmol) in toluene (150 mL) in several portions over 2 h. The mixture was stirred at 23° C. for 25 h. The volatiles were removed under vacuum and the residue was extracted with hexanes (50 mL) and benzene (2×70 mL). The extracts were combined and the volatiles were removed under vacuum yielding pure Zr(NMePh)₄ as a pale yellow powder (yield 2.18 g, 45%). Anal. Calcd for C₂₈H₃₂N₄Zr: C, 65.19; H, 6.27; N, 10.86. Found: C, 64.82; H, 6.40; N, 10.47. ¹H NMR (C₆D₆): δ 7.11 (t, J=7.2, 2H, Ph), 6.86 (d, J=7.2, 2H, Ph), 6.77 (t, J=7.2, 1H, Ph), 2.97 (s, 3H, NMe). 13C {1H} NMR (C₆D₆): δ 151.9, 129.9, 120.6, 116.3, 32.8.

Example 12

Synthesis of Zr(NMePh)₂Cl₂(THF)₂

A slurry of Zr(NMePh)₄ (1.16 g, 2.24 mmol) and ZrCl₄ (0.520 g, 2.24 mmol) in a mixture of Et₂O (60 mL) and THF (25 mL) was stirred at 23° C. for 5 h. The mixture was filtered to afford a yellow solid and clear yellow filtrate. The solid was dried under vacuum overnight and identified as Zr(NMePh)₂Cl₂(THF)₂ (1.46 g). The yellow filtrate was cooled to −60° C. for 3 d yielding yellow crystals (0.40 g). Total yield 80%. Single crystals suitable for X-ray diffraction were obtained by crystallization from toluene (−20° C.) for several days. Anal. Calcd for C₂₂H₃₂Cl₂N₂O₂Zr: C, 50.94; H, 6.23; N, 5.40. Found: C, 50.48; H, 6.51; N, 5.16. ¹H NMR (THF-d8): δ 7.24 (d, J=7.2, 2H, Ph), 7.13 (t, J=7.2, 2H, Ph), 6.70 (t, J=7.2, 1H, Ph), 3.61 (m, 4H, THF), 3.30 (s, 3H, NMe), 1.76 (m, 4H, THF). $^{13}C\{^1H\}$ NMR (THF-d8): δ 154.4, 128.8, 120.0, 118.6, 67.4 (THF), 36.2 (NMe), 26.1 (THF).

Example 13

Synthesis of (MBSBI)Zr(NMePh)$_2$

NMR scale: A solution of Zr(NMePh)$_2$Cl$_2$(THF)$_2$ (0.030 g, 0.058 mmol) in C$_6$D$_6$ (0.6 mL) was added to solid Li$_2$[MBSBI]Et$_2$O (0.030 g, 0.059 mmol). The yellow-orange slurry was stirred for 19 h, centrifuged upside down to trap the LiCl at the top of the tube, and a $^1$H NMR spectrum was recorded. The spectrum established that the product mixture consisted of rac-(MBSBI)Zr(NMePh)$_2$, meso-(MBSBI)Zr(NMePh)$_2$ and (MBSBI){Zr(NMePh)$_2$Cl}$_2$ in a 2:2:1.5 molar ratio. This reaction was repeated in Et$_2$O (17 h, 23° C.) and the product distribution was determined by removal of the solvent under vacuum and NMR analysis of the crude product in C$_6$D$_6$. The same products were observed in a 2/2/1.5 molar ratio.

Preparative scale: A slurry of Zr(NMePh)$_2$Cl2(THF)$_2$ (0.573 g, 1.11 mmol) and Li$_2$[MBSBI]Et$_2$O (0.531 g, 1.04 mmol) in Et$_2$O (80 mL) was stirred for 18 h at 23° C. The color changed from yellow to red. The mixture was filtered to yield a red precipitate and a red filtrate. The filtrate was taken to dryness under vacuum, yielding a red solid (230 mg). NMR analysis established that the red solid contained (MBSBI)Zr(NMePh)$_2$ (rac/meso=7.2) and (MBSBI){Zr(NMePh)$_2$Cl}$_2$ in a molar ratio of 7/3. The red solid was recrystallized from Et$_2$O afford pure (MBSBI)Zr(NMePh)$_2$ (170 mg rac/meso=9.5). The precipitate from the first filtration was extracted with toluene (2×40 mL). The volatiles were removed from the extracts under vacuum to yield analytically pure (MBSBI)Zr(NMePh)$_2$ (rac/meso=1/17) as a red solid (208 mg). Pure meso-(MBSBI)Zr(NMePh)$_2$ (100 mg) was isolated by recrystallizaion of the 1/17 mixture of rac and meso-(MBSBI)Zr(NMePh)$_2$ (200 mg) from toluene. Total yield for (MBSBI)Zr(NMePh)$_2$ 51%. Anal. Calcd for C$_{44}$H$_{42}$N$_2$SiZr: C, 73.58; H, 5.91; N, 3.90. Found: C, 73.48 ; H, 6.15 ; N, 3.10. Data for rac-(MBSBI)Zr(NMePh)$_2$. $^1$H NMR (C$_6$D$_6$): δ 8.10 (dd, J=7.2, 3, 2H, indenyl), 7.79 (d, J=7.2, 2H, indenyl), 7.55 (m, 2H, indenyl), 7.35 (d, J=10.8, 2H, indenyl), 7.27–7.22 (m, 8H, indenyl+Ph), 6.96 (tt, J=7.2, 1, 2H, Ph), 6.86 (d, J=7.2, 4H, Ph), 6.74 (s, 2H, H3), 2.26 (s, 6H), 2.05 (s, 6H), 0.87 (s, 6H, SiMe$_2$). Data for meso-(MBSBI)Zr(NMePh)$_2$: $^1$H NMR (C$_6$D$_6$, 50° C.): δ 7.96 (d, J=8.6, 2H, indenyl), 7.71 (d, J=7.2, 2H, indenyl), 7.35 (d, J=7.2, 2H), 7.18–7.06 (m, 9H), 6.98 (t, J=7.2, 2H, Ph), 6.93–6.83 (m, 3H), 6.58 (td, J=7.2, 3.6, 1H, Ph), 6.28 (dd, J=7.2, 3.6, 3H), 3.87 (s, 3H, NMe), 2.21 (s, 6H, 2-Me), 1.15 (s, 3H, SiMe$_2$), 0.80 (s, 3H, SiMe$_2$), 0.17 (s, 3H, NMe).

Example 14

Synthesis of Li$_2$[PhNCH$_2$CH$_2$NPh](Et$_2$O)

A solution of "BuLi in hexanes (16.3 mL, 2.5 M, 40.7 mmol) was added to a solution of PhNHCH$_2$CH$_2$NHPh (4.32 g, 20.4 mmol) in Et$_2$O (70 mL) over 5 min by syringe at 23° C. The resulting slurry was stirred for 48 h and filtered. The pale yellow solid was washed with hexanes (70 mL) and dried under vacuum (4.14 g, 91%). $^1$H NMR (THF-d$_8$): δ 6.68 (t, J=8, 4H,Ph), 6.36 (br s, 4H, Ph), 5.79 (t, J=8, 2H, Ph), 3.38 (q, J=7, 4H, Et$_2$O), 3.32 (br s, 4H, NCH$_2$), 1.12 (t, J=7, 6H, Et$_2$O).

Example 15

Synthesis of Zr(PhNCH$_2$CH$_2$NPh)$_2$

An off-white slurry of Li$_2$[PhNCH$_2$CH$_2$NPh](Et$_2$O) (3.35 g, 10.7 mmol) in toluene (100 mL) was prepared and ZrCl$_4$ (1.24 g, 5.33 mmol) was added in several portions over 1 h. The mixture was stirred at 23° C. for 42 h. The supernatant was removed and THF (50 mL) was added to the residue. The mixture was stirred for 5 h and the volatiles were removed under vacuum. The resulting solid was extracted with benzene (40 mL). The volatiles were removed from the extract under vacuum and benzene was added to the resulting solid. The mixture was stirred for 30 min and filtered. The yellow solid was washed with benzene (10 mL) and dried under vacuum (1.76 g, 64%). Anal. Calcd for C$_{28}$H$_{28}$N$_4$Zr: C, 65.70; H. 5.53; N, 10.95. Found: C, 62.35; H, 5.23 ; N, 9.92. $^1$H NMR (THF-d8): δ 6.99 (t, J=7.2, 8H, m-Ph), 6.76 (d, J=7.2, 8H, o-Ph), 6.52 (t, J=7.2, 4H, p-Ph), 3.91 (br.s, 8H, CH$_2$CH$_2$). $^{13}C\{^1H\}$ NMR (THF-d8): δ 156.8, 128.9, 118.0, 113.2, 54.3 (CH$_2$CH$_2$).

Example 16

Synthesis of {Zr(PhNCH$_2$CH$_2$NPh)Cl$_2$(THF)}$_2$

A slurry of Zr(PhNCH$_2$CH$_2$NPh)$_2$ (0.512 g, 1.00 mmol) and ZrCl$_4$ (0.233 g, 1.00 mmol) in a mixture of Et$_2$O (25 mL) and THF (10 mL) was stirred at 23° C. for 5.5 h. The mixture was a clear yellow solution. The solution was concentrated to ca. 10 mL and cooled to −20° C. for 9 h. No solid was formed. The volatiles were removed under vacuum. The resulting yellow soild was dissolved in benzene (10 mL) and the volatiles were removed under vacuum. The solid was taken up in a mixture of toluene (5 mL) and benzene (5 mL), stirred for 10 min and filtered. The resulting yellow-orange solid was dried under vacuum (yield 0.47 g, 63%). Single crystals suitable for X-ray diffraction were obtained by diffusion of hexanes into a CH$_2$Cl$_2$ solution at 23° C. for several days. $^1$H NMR (THF-d8): δ 7.18 (t, J=7.2, 4H, Ph), 7.05 (d, J=7.2, 4H, Ph), 6.77 (t, J=7.2, 2H, Ph), 4.08 (s, 4H, CH$_2$CH$_2$), 3.63 (m, 4H, THF), 1.78 (m, 4H, THF). Anal. Calcd for C18H22Cl2N2OZr: C, 48.63; H, 5.00; N, 6.30; Cl, 15.95. Found: C, 48.77; H, 5.05; N, 6.15; Cl, 15.64.

Example 17

Synthesis of (MBSBI)Zr(PhNCH$_2$CH$_2$NPh)

A flask was charged with {Zr(PhNCH$_2$CH$_2$NPh)Cl$_2$(THF)}$_2$ (0.458 g, 1.06 mmol) and Li$_2$[MBSBI](Et$_2$O) (0.544 g, 1.06 mmol), and THF (50 mL) was added by vacuum transfer at −78° C. The mixture was stirred for 9 h during which time the bath was allowed to warm to 5° C. The volatiles were removed under vacuum. The resulting solid was taken up in benzene (50 mL) and filtered. The precipitate was washed with benzene (10 mL). The filtrate and wash were combined and the volatiles were removed under vacuum. The benzene extraction process was repeated and the final solid was dried at 50° C. under vacuum to afford a red solid (682 mg, rac/meso=2/1). This crude product was dissolved in toluene, precipitated with hexanes, isolated by filtration and dried under vacuum to afford pure rac-(MBSBI)Zr(PhNCH$_2$CH$_2$NPh) (332 mg, 44%). Single crystals of meso-(MBSBI)Zr(PhNCH$_2$CH$_2$NPh)$_2$ for X-ray analysis were grown slow evaporation of the filtrate. Anal. Calcd for C$_{44}$H$_{42}$N$_2$SiZr: C, 73.74; H. 5.64; N, 3.91. Found: C, 72.92 ; H, 5.84 ; N, 3.76. Data for rac-(MBSBI)Zr(PhNCH$_2$CH$_2$NPh)$_2$: $^1$H NMR (C$_6$D$_6$): δ 7.91 (d, J=7.2, 2H, indenyl), 7.38–7.24 (m, 6H), 7.11–7.06 (m, 6H), 7.00 (s, 2H, indenyl), 6.82 (t, J=7.2, 2H), 6.17 (d, J=7.2, 4H), 3.76 (d, J=7.2, 2H, CH$_2$), 2.72 (d, J=7.2, 2H, CH$_2$), 2.35 (s, 6H, 2-Me), 0.94 (s, 6H, SiMe$_2$). Data for meso-(MBSBI)Zr(PhNCH$_2$CH$_2$NPh)$_2$: $^1$H NMR (C$_6$D$_6$): δ 7.91 (d, J=7.2, 2H, indenyl), 7.83 (d, J=8, 2H,idenyl), 7.38–7.05 (m, 16H), 6.94

(s, 2H, indenyl), 6.30 (d, J=8, 2H), 4.05 (t, J=6, 2H, CH$_2$), 3.37 (t, J=6, 2H, CH$_2$), 2.18 (s, 6H, 2-Me), 1.15 (s, 3H, SiMe$_2$), 0.78 (s, 3H, SiMe$_2$).

Having described the invention with reference to particular compositions, methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A process of synthesizing an ansa-metallocene complex of the formula:

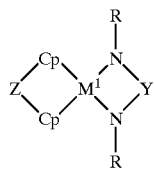

wherein Cp independently and in each occurrence is a cyclopentadienyl, indenyl, fluorenyl, or related group that can Π-bond to the metal, or hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl, or related group, Z is a bridging group which links the Cp groups, M$^1$ is a group 4 metal, R is a hydrogen, hydrocarbyl group having from 1 to 40 carbon atoms, or silyl group, or substituted derivative of said hydrocarbyl or silyl group wherein each R may be the same or different, Y is a bridging group that links the two NR groups, said process comprising:
reacting a chelated bisamide group 4 metal complex with an ansa-bis-cyclopentadienyl dianion reagent to provide said ansa-metallocene complex.

2. The process of claim 1 wherein said Group 4 metal is selected from the group consisting of titanium, zirconium, and hafnium.

3. The process of claim 2 wherein said Group 4 metal is zirconium.

4. The process of claim 1 wherein said substituted derivative of R may contain substituents from the group consisting of alkyl, aryl, silyl, haloalkyl, haloaryl, and halosilyl.

5. The process of claim 1 wherein R is phenyl.

6. The process of claim 1 wherein Y is —CH$_2$CH$_2$CH$_2$—.

7. The process of claim 1 wherein Z is selected from the group of bridges consisting of silylene, substituted silylene, benzo, substituted benzo, methylene, substituted methylene, ethylene, and substituted ethylene.

8. The process of claim 7 wherein said bridge is substituted silylene and said substituted silylene is SiMe$_2$.

9. The process of claim 1 wherein Cp is selected from the group consisting of indenyl and hydrocarbyl substituted indenyl.

10. The process of claim 1 wherein said chelated bisamide group 4 metal complex is of the general formula M$^1$X$_2$L$_n$(RN—Y—NR)

wherein M$^1$ is a Group 4 metal,

X is a leaving group that can be displaced by a cyclopentadienyl ligand wherein each X can be the same or different or linked, L is independently and in each occurrence a Lewis base, n is a whole number from 0–4, R is a hydrogen, hydrocarbyl group having from 1 to 40 carbon atoms, or silyl group, or substituted derivative of said hydrocarbyl or silyl group and each R can be the same or different, and Y is a bridging group which links the two NR groups.

11. The process of claim 10 wherein X is selected from the group consisting of halogen, carboxylate, acetate, trifluoroacetate, diketonate, triflate, and nitrate.

12. The process of claim 11 wherein X is a halogen and said halogen is chloride.

13. The process of claim 10 wherein L is selected from the group consisting of ethers, amines, and pyridines.

14. The process of claim 13 wherein L is an ether and said ether is tetrahydrofuran.

15. The process of claim 10 wherein said chelated bisamide group 4 metal complex is Zr(PhNCH$_2$CH$_2$CH$_2$NPh)Cl$_2$(THF)$_2$.

16. The process of claim 1 wherein said ansa-bis-cyclopentadienyl dianion reagent is of the general formula (M$^2$—Cp—Z—Cp—M$^2$)(L)$_m$ wherein M$^2$ is a group 1 metal or both M$^2$ together can be a group 2 metal, Cp is independently and in each occurrence is a cyclopentadienyl, indenyl, fluorenyl, or related group that can Π-bond to the metal, or hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl, or related group, Z is a bridging group which links the Cp groups, L is independently and in each occurrence a Lewis base, and m is 0–8.

17. The process of claim 16 wherein Cp is indenyl or a substituted derivative of indenyl.

18. The process of claim 17 wherein said ansa-bis-cyclopentadienyl dianion reagent is a lithium ansa-bis-indenyl.

19. The process of claim 18 wherein said lithium ansa-bis-indenyl is Li$_2$(1-indenyl)$_2$SiMe$_2$(Et$_2$O).

20. The process of claim 18 wherein said lithium ansa-bis-indenyl is Li$_2$(2-methyl-1-indenyl)$_2$SiMe$_2$(Et$_2$O).

21. The process of claim 18 wherein said lithium ansa-bis-indenyl is Li$_2$(2-methyl-4,5-benz-1-indenyl)$_2$SiMe$_2$(Et$_2$O).

22. The process of claim 18 wherein said lithium ansa-bis-indenyl is Li$_2$(2-methyl-4-phenyl-1-indenyl)$_2$SiMe$_2$(Et$_2$O).

23. The process of claim 1 wherein said process is conducted at a temperature from about −80° C. to about 200° C.

24. The process of claim 23 wherein said temperature is about 0° C. to about 100° C.

25. The process of claim 24 wherein said temperature is about 25° C.

26. The process of claim 1 wherein the reaction is conducted in the presence of a nonaqueous, nonalcoholic solvent.

27. The process of claim 26 wherein said solvent is selected from the group consisting of hydrocarbons and ethers.

28. The process of claim 27 wherein said hydrocarbon is selected from the group consisting of benzene, toluene, hexane, and heptane.

29. The process of claim 27 wherein said ether is selected from the group consisting of diethyl ether and tetrahydrofuran.

30. The process of claim 29 wherein said ether is diethyl ether.

31. The process of claim 1 wherein an excess of said ansa-bis-cyclopentadienyl dianion reagent is used.

32. The process of claim 1 further comprising isolating said ansa-metallocene complex from the reaction mixture.

33. The process of claim 1 further comprising converting said ansa-metallocene complex to a derivative.

34. The process of claim 33 wherein said derivative is a dichloride.

35. The process of claim 33 wherein said derivative is a dialkyl.

36. A process of synthesizing a racemic ansa-metallocene complex of the formula:

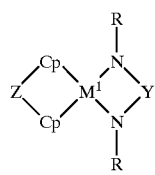

wherein Cp independently and in each occurrence is cyclopentadienyl, indenyl, fluorenyl, or related group that can Π-bond to the metal, or hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl, or related group, Z is a bridging group which links the Cp groups, $M^1$ is a group 4 metal, R is a hydrogen, hydrocarbyl group having from 1 to 40 carbon atoms, or silyl group, or substituted derivative of said hydrocarbyl or silyl group wherein each R may be the same or different, Y is the bridging group that links the two NR groups, said process comprising:

reacting a chelated bisamide group 4 metal complex with an ansa-bis-cyclopentadienyl dianion reagent to provide said racemic ansa-metallocene complex.

37. The process of claim 36 wherein said group 4 metal is zirconium.

38. The process of claim 36 wherein R is phenyl.

39. The process of claim 36 wherein Y is —$CH_2CH_2CH_2$—.

40. The process of claim 36 wherein Z is $SiMe_2$.

41. The process of claim 36 wherein said chelated bisamide group 4 metal complex is $Zr(PhNCH_2CH_2CH_2NPh)Cl_2(THF)_2$.

42. The process of claim 36 wherein said ansa-bis-cyclopentadienyl dianion reagent is a lithium ansa-bis-indenyl.

43. The process of claim 42 wherein said lithium ansa-bis-indenyl is $Li_2(1\text{-indenyl})_2SiMe_2(Et_2O)$.

44. The process of claim 42 wherein said lithium ansa-bis-indenyl is $Li_2(2\text{-methyl-1-indenyl})_2SiMe_2(Et_2O)$.

45. The process of claim 42 wherein said lithium ansa-bis-indenyl is $Li_2(2\text{-methyl-4,5-benz-1-indenyl})_2SiMe_2(Et_2O)$.

46. The process of claim 42 wherein said lithium ansa-bis-indenyl is $Li_2(2\text{-methyl-4-phenyl-1-indenyl})_2SiMe_2(Et_2O)$.

47. The process of claim 36 further comprising converting the racemic ansa-metallocene to a derivative.

48. The process of claim 47 wherein the derivative is a dichloride.

49. The process of claim 47 wherein the derivative is a dialkyl.

50. The process of claim 36 further comprising isolating said racemic ansa-metallocene complex from the reaction mixture.

* * * * *